United States Patent
Tsuchikura et al.

(10) Patent No.: US 10,070,949 B2
(45) Date of Patent: Sep. 11, 2018

(54) VASCULAR PROSTHESIS

(71) Applicant: Toray Industries, Inc., Tokyo (JP)

(72) Inventors: Hiroshi Tsuchikura, Otsu (JP); Satoshi Yamada, Otsu (JP); Koji Kadowaki, Otsu (JP); Atsushi Kuwabara, Otsu (JP)

(73) Assignee: Toray Industries, Inc. (JP)

(*) Notice: Subject to any disclaimer, the term of this patent is extended or adjusted under 35 U.S.C. 154(b) by 46 days.

(21) Appl. No.: 15/100,109

(22) PCT Filed: Nov. 26, 2014

(86) PCT No.: PCT/JP2014/081214
§ 371 (c)(1),
(2) Date: May 27, 2016

(87) PCT Pub. No.: WO2015/080143
PCT Pub. Date: Jun. 4, 2015

(65) Prior Publication Data
US 2017/0035546 A1 Feb. 9, 2017

(30) Foreign Application Priority Data
Nov. 29, 2013 (JP) .................................. 2013-248492

(51) Int. Cl.
A61F 2/06 (2013.01)
A61L 27/50 (2006.01)
A61F 2/00 (2006.01)
A61F 2/07 (2013.01)

(52) U.S. Cl.
CPC .............. *A61F 2/06* (2013.01); *A61F 2/0077* (2013.01); *A61F 2/07* (2013.01); *A61L 27/507* (2013.01); *A61F 2002/0086* (2013.01); *A61F 2210/0076* (2013.01); *A61F 2230/0069* (2013.01); *A61F 2240/001* (2013.01)

(58) Field of Classification Search
CPC .............. A61L 27/507; D03D 15/0061; D03D 13/008; D03D 1/00; D03D 3/02; D03D 11/00; D03D 15/00; D03D 15/0088; D10B 2509/06; A61F 2/07; A61F 2/06; A61F 2210/0076; A61F 2250/0017; D04B 21/16; B29C 51/004; B32B 2250/20; B32B 2262/0276; B32B 5/024
USPC .................. 428/36.1, 361; 139/387
See application file for complete search history.

(56) References Cited

U.S. PATENT DOCUMENTS

| 3,350,488 A | 10/1967 | Breen |
| 3,531,368 A | 9/1970 | Okamoto et al. |
| 5,697,969 A | 12/1997 | Schmitt et al. |
| 5,883,022 A * | 3/1999 | Elsener .................. A47K 10/02 442/189 |
| 9,943,424 B2 * | 4/2018 | Yamada .................... A61F 2/89 |
| 2006/0009835 A1 | 1/2006 | Osborne et al. |
| 2006/0009839 A1 | 1/2006 | Tan |
| 2011/0129657 A1 * | 6/2011 | Clough .................. B32B 5/024 428/219 |
| 2012/0171917 A1 * | 7/2012 | Rasmussen .............. A61F 2/07 442/199 |
| 2013/0035014 A1 * | 2/2013 | Tone .................... D03D 13/008 442/189 |
| 2013/0041452 A1 | 2/2013 | Fujita et al. |
| 2015/0203995 A1 * | 7/2015 | Adams ................ D03D 1/0035 2/455 |
| 2016/0058588 A1 | 3/2016 | Yamada et al. |
| 2016/0135944 A1 * | 5/2016 | Saito ........................ A61F 2/07 623/1.13 |
| 2017/0182752 A1 * | 6/2017 | Callhoff .................. B32B 27/32 |
| 2017/0183873 A1 * | 6/2017 | Vido ...................... E04D 12/002 |
| 2017/0252617 A1 * | 9/2017 | Caron Kardos ....... A63B 60/48 |

FOREIGN PATENT DOCUMENTS

| EP | 0 855 170 | 7/1998 |
| JP | 61-004546 A | 1/1986 |
| JP | 61-058190 B2 | 12/1986 |
| JP | 2749447 B2 | 2/1998 |
| JP | 2005-124959 A | 5/2005 |
| JP | 2008-505713 A | 2/2008 |
| JP | 2008-505728 A | 2/2008 |
| JP | 2011-245283 A | 12/2011 |
| JP | 2012-139498 A | 7/2012 |
| RU | 2 469 133 | 12/2012 |
| WO | 2010/080126 | 7/2010 |
| WO | 2011/136243 A1 | 11/2011 |
| WO | 2013/087898 | 6/2013 |
| WO | 2014/175301 A1 | 10/2014 |
| WO | 2015/005105 A1 | 1/2015 |

OTHER PUBLICATIONS

Supplementary European Search Report dated Jun. 9, 2017, of corresponding European Application No. 14865061.7.

\* cited by examiner

*Primary Examiner* — Seema Mathew
(74) *Attorney, Agent, or Firm* — DLA Piper LLP (US)

(57) ABSTRACT

A vascular prosthesis with tubular woven structure, the prosthesis includes an inner layer adapted to contact a blood flow, the inner layer being formed of warp and weft yarns and having a cover factor of 1800 or more, each of a warp and weft yarns including a microfiber multifilament yarn with a monofilament fineness of 0.50 dtex or less, the multifilament yarn including microfiber monofilaments having an average intersecting angle S of the monofilaments of less than 25°.

12 Claims, No Drawings

VASCULAR PROSTHESIS

TECHNICAL FIELD

This disclosure relates to a vascular prosthesis. In particular, the disclosure relates to a textile vascular prosthesis with tubular woven structure, the prosthesis being highly effective in promoting the settlement of adherent vascular endothelial cells.

BACKGROUND

Vascular prostheses are used in adults mainly to replace pathological blood vessels in the body and create a bypass or a shunt, and are used in children mainly to create a shunt. Vascular prostheses are thus required to be highly biocompatible and non-toxic, durable and non-degradable in living bodies, flexible, substantially non-permeable to blood, and highly effective in promoting the settlement of adherent vascular endothelial cells.

Vascular endothelial cells constantly produce nitrogen monoxide and prostaglandin to inhibit platelet aggregation. Prostaglandin is a substance that controls platelet function and the coagulation and fibrinolytic system to prevent thrombus formation in the blood vessels. Hence, high effectiveness in promoting the settlement of adherent vascular endothelial cells is a very important characteristic of vascular prostheses.

Conventional textile vascular prostheses are typically made of a woven or knitted fabric of chemical fibers such as polyester. Many of them are made of a very high density woven or knitted fabric, i.e., a tightly woven or knitted fabric to prevent leakage of blood through their walls and maintain their shapes. However, conventional textile vascular prostheses suffer from slow and uneven formation of a vascular endothelial cell layer. That is, in conventional textile vascular prostheses, thick fibers are tightly woven or knitted, which provides only a few scaffolds for formation of a vascular endothelial cell layer. In addition, even though some cells adhere to the inner wall, most of them tend to be easily washed away by the blood flow, which may result in formation of an occluding thrombus in a narrow blood vessel in the periphery.

Various proposals have been made to enhance the settlement of adherent vascular endothelial cells in vascular prostheses. One of the proposals is, for example, a vascular prosthesis having raised microfibers of 0.5 denier or less on the inner wall as described in JP 61-4546 B. Another proposal is a vascular prosthesis having raised microfibers of 0.5 denier or less on the inner wall and/or the outer wall and comprising a ground structure made from a ground yarn containing fibers of 1.0 denier or more as described in JP 61-58190 B.

However, formation of raised microfibers on the inner wall, as described in JP '546 and JP '190, does not sufficiently enhance the settlement of adherent cells. The raised fibers may inversely inhibit the growth of the adherent cells.

JP 2011-245283 A describes a microfiber woven fabric to be used for a stent graft. However, use of that woven fabric for a vascular prosthesis without applying any modifications does not sufficiently improve the settlement of adherent cells, the leakage of blood or kink resistance. JP 2012-139498 A describes a woven fabric with good biocompatibility. The woven fabric does not adversely affect the living body. However, the woven fabric contains no microfibers and, therefore, use of the woven fabric for a vascular prosthesis without applying any modifications does not sufficiently improve the settlement of adherent cells, the leakage of blood or kink resistance.

It could therefore be helpful to provide a vascular prosthesis having various properties required of it and is highly effective in promoting settlement of adherent vascular endothelial cells.

SUMMARY

We found a textile structure that is highly effective in promoting the adherence of vascular endothelial cells and their growth, i.e., the settlement of adherent vascular endothelial cells. We thus provide:

(1) A vascular prosthesis with tubular woven structure, the prosthesis comprising an inner layer to be in contact with a blood flow, the inner layer being formed of warp and weft yarns and having a cover factor of 1800 or more, each of the warp and weft yarns comprising a microfiber multifilament yarn with a monofilament fineness of 0.50 dtex or less, the multifilament yarn comprising microfiber monofilaments having an average intersecting angle S of the monofilaments of less than 25°.

(2) The vascular prosthesis of the above (1), which comprises the microfiber multifilament yarn in an amount of 50% by weight or more in each of the warp and weft.

(3) The vascular prosthesis of the above (1) or (2), wherein the cover factor defined by the warp and weft yarns forming the inner layer is 2000 or more.

(4) The vascular prosthesis of any of the above (1) to (3), wherein the tubular woven structure comprises two or more layers, and one or more of the layers other than the inner layer comprise a multifilament yarn with a monofilament fineness of 1.0 dtex or more in the warp.

(5) The vascular prosthesis of any of the above (1) to (4), wherein the tubular woven structure comprises two or more layers, and one or more of the layers other than the inner layer comprise a monofilament yarn with a monofilament fineness of 20.0 dtex or more in the weft.

The vascular prosthesis with the above structure has various properties required of it and is highly effective in promoting settlement of adherent vascular endothelial cells.

DETAILED DESCRIPTION

Preclotting

Blood pressure is maintained at a certain high level in a living body and, due to this, leakage of blood through the voids between the fibers is difficult to avoid. Accordingly, before use of a textile vascular prosthesis in vascular surgery, so-called preclotting is often performed. Preclotting is a pre-implantation procedure in which a vascular prosthesis is brought into contact with blood for artificial formation of thrombi and temporal clogging of the voids between the fibers with the thrombi.

In today's surgical operations, however, heparin is often used to prevent coagulation of the blood. Consequently, it is often the case that clogging by preclotting becomes insufficient, which leads to a risk that the leakage of blood may occur and may result in massive bleeding after surgery. Another risk is that, after surgery, fibrin produced by preclotting may begin to be dissolved by fibrinolysis as a natural phenomenon and then the coagulated blood tissue may be easily broken.

Accordingly, when a medical textile material is used in aortic and cardiac surgery using a large amount of heparin, a biodegradable substance such as collagen and gelatin is applied to the textile material to prevent leakage of blood by not allowing permeation of the blood into the textile material. This technique is utilized for the so-called coated vascular prosthesis and the so-called coated prosthetic patch, and they are already commercially available. However, since many of the substances (such as collagen and gelatin) used to create clogging on the surface of a coated vascular prosthesis or a coated prosthetic patch are naturally occurring substances, stabilization of the quality of the substances is very difficult. Therefore, these substances are not suitable for industrial application.

Use of Microfibers to Prevent Leakage of Blood

Before describing how the vascular prosthesis effectively promotes the settlement of adherent vascular endothelial cells, an assumed mechanism of prevention of the leakage of blood by microfibers will be described below.

Blood coagulation starts from fibrin formation and platelet aggregation. Fibrin formation is affected by heparin administration or fibrinolysis as described above, whereas platelet aggregation is less affected by them. Based on this, we attempted to utilize the platelet aggregation pathway by focusing on the diameter of the structural fibers of the vascular prosthesis.

Platelets that contact a foreign body other than the surface of vascular endothelial cells adhere to the surface of the foreign body. When the stimulus from the foreign body is large, platelets rupture and release their internal granules into the surroundings, and the platelet debris adheres to the site where they rupture. The spread granules adhere to other platelets and stimulate them to rupture and release their granules like a chain reaction. The ruptured platelets leave debris. The debris and granules gather one after another and aggregate to form a thrombus. Since the size of platelets is about 1 to 2 μm, a microfiber multifilament yarn with a monofilament fineness of 0.50 dtex (corresponding to filament diameter of about 8 μm) or less will easily capture platelets. A microfiber multifilament yarn with a monofilament fineness of 0.30 dtex (corresponding to filament diameter of 5 μm) or less has smaller spaces between the monofilaments and will much easily capture platelets. In this manner, a thrombus grown by the above mechanism adheres to the ultra-fine microfiber multifilament yarn. Once platelet aggregation is started, fibrin formation is spontaneously induced. Consequently, leakage of blood is effectively prevented.

Settlement of Adherent Vascular Endothelial Cells and the Diameter of Structural Fibers of the Inner Layer of Vascular Prosthesis For settlement of adherent vascular endothelial cells, prevention of the leakage of blood is first required. Leakage of blood is prevented by the above-described mechanism utilizing platelet aggregation and fibrin formation. The vascular prosthesis comprising a microfiber multifilament yarn with a monofilament fineness of 0.50 dtex or less, preferably 0.30 dtex or less, in each of the warp and weft forming the inner layer provides a very large number of scaffolds suitable for adherence of vascular endothelial cells. As a result, vascular endothelial cells are well settled on the structural fibers of the inner layer of the vascular prosthesis, and vascular endothelial cells adhere well to the inner layer of the vascular prosthesis. In addition, since the microfiber multifilament yarn is contained in both of the warp and weft, the adherent vascular endothelial cells grow and freely spread over the fiber surface of the warp and weft of the inner layer of the vascular prosthesis, thereby forming a thin layer of vascular endothelial cells inside the vascular prosthesis. Inversely, when the monofilament fineness is 0.008 dtex or less, adherence of the cells tends to be inhibited. Preferably, the monofilament fineness is 0.02 to 0.25 dtex.

Content Ratio of Microfiber Multifilament Yarn in Warp and Weft

Growth of vascular endothelial cells is further enhanced when each of the warp and weft of the inner layer to be in contact with the blood flow contains a microfiber multifilament yarn in an amount of 50% by weight or more relative to the total amount of the fibers forming the inner layer. When the amount (%) of the microfiber multifilament yarn contained in each of the warp and weft of the inner layer is less than 50% by weight relative to the total amount of the fibers forming the inner layer, fewer scaffolds are provided for adherence and growth of vascular endothelial cells, resulting in slow growth of vascular endothelial cells. For this reason, a larger amount of the microfiber multifilament yarn relative to the total amount of the fibers forming the inner layer is better. More preferably, each of the warp and weft forming the inner layer contains a microfiber multifilament yarn in an amount of 80% by weight or more, further preferably in an amount of 100% by weight.

Average Intersecting Angle of Microfiber Monofilaments

Adherent vascular endothelial cells grow along the direction where the microfiber monofilaments lie. Hence, when the microfiber monofilaments are oriented in the same direction, vascular endothelial cells will easily grow along the direction of the oriented microfiber monofilaments. To achieve this, the average angle at which the microfiber monofilaments intersect (average intersecting angle S) within the microfiber multifilament yarn is preferably less than 25°. An average intersecting angle S of the microfiber monofilaments of 25° or more indicates varying directions of the monofilaments, which will result in slow growth of vascular endothelial cells. To orient the microfiber monofilaments in the same direction, care should be taken during the production process of the tubular woven fabric to avoid disturbance of the orientation of the monofilaments, which is manifested by breakage of the microfiber multifilament yarn and formation of lint. Preferably, the microfiber multifilament yarn is not subjected to external force applied by, for example, nap raising, loop formation, water-jet punching and the like. The average intersecting angle S is most preferably zero degrees.

Cover Factor

The cover factor defined by the warp and weft yarns forming the inner layer is preferably 1800 or more. The cover factor is more preferably 2000 or more. The cover factor indicates the degree of the presence of voids between the fibers (packing density). A smaller cover factor means a larger amount of voids between the fibers. When the cover factor defined by the warp and weft yarns is 1800 or more, the microfiber multifilament yarn is densely laid throughout the surface, which enhances the adherence and growth of vascular endothelial cells and promotes settlement of the adherent vascular endothelial cells. When the cover factor defined by the warp and weft yarns is 2000 or more, leakage of blood is more efficiently prevented and leakage of blood during transplantation is reduced. A higher cover factor is preferred for settlement of adherent vascular endothelial cells, but a too high cover factor will deteriorate the flexibility of the vascular prosthesis and reduce weaving efficiency during production of the vascular prosthesis. The maximum value of the cover factor will vary depending on the stiffness of the fibers to be used, the performance of the loom to be used, and the weave pattern to be used, but typically the cover factor is preferably 4000 or less.

The vascular prosthesis with tubular woven structure preferably comprises two or more layers. Such a structure comprising two or more layers is advantageous because each layer can be provided with a different woven design, which allows further enhancement of the performance required of the vascular prosthesis. Examples of when the tubular woven structure is provided with two layers or more for enhancement of the performance of the vascular prosthesis will be described below. However, the following examples are provided merely for the purpose of illustrating preferred examples, and do not limit the tubular woven structure. Vascular prosthesis in which one or more of layers other than the inner layer comprise multifilament yarn with monofilament fineness of 1.0 dtex or more in the warp The mechanical strength of the vascular prosthesis is high when the tubular woven structure comprises two or more layers and one or more of the layers other than the inner layer comprise a multifilament yarn with a monofilament fineness of 1.0 dtex or more in the warp. The mechanical strength of the vascular prosthesis tends to decrease when a multifilament yarn with a monofilament fineness of 1.0 dtex or more is not contained in the warp. In particular, in long-term use of the implant, deterioration of the strength due to hydrolysis is concerned, depending on the type of the polymer used as the material of the fibers and, therefore, the warp preferably comprise a multifilament yarn with a monofilament fineness of 2.0 dtex or more. Exposure of the multifilament yarn on the surface of the inner layer is not preferred because the exposed multifilament yarn will inhibit the growth of endothelial cells and serve as the starting point of the leakage of blood and thrombus formation.

Vascular Prosthesis in which One or More of Layers Other than the Inner Layer Comprise a Monofilament Yarn with Monofilament Fineness of 20.0 Dtex or More in the Weft When the tubular woven structure comprises two or more layers and one or more of the layers other than the inner layer comprise a monofilament yarn with a monofilament fineness of 20.0 dtex or more in the weft, the shape of the vascular prosthesis is maintained, elasticity is high and kinking is prevented (kink resistance is high). To more efficiently achieve these effects, the monofilament yarn forming the layers other than the inner layer is preferably arranged in a spiral manner. With this arrangement, the vascular prosthesis does not need to have a crimped structure such as those provided to conventional vascular prostheses, and yet has the same levels of shape-retaining properties and self-expansion properties as conventional vascular prostheses with a crimped structure.

The microfiber multifilament yarn may be a single type or a combination of different types of microfiber multifilament yarns with different monofilament finenesses and different total finenesses.

As the microfiber multifilament yarn, the so-called direct spun yarn may be directly used, and a splittable yarn may be used. The splittable yarn may be the one that can be made into ultra-fine fibers by chemical or physical means. The ultra-fining process may be performed after the tubular woven fabric is formed. The ultra-fining process by chemical or physical means may be done by, for example, removing one of the components in composite fibers or splitting composite fibers into their respective component, thereby giving fibrils or ultra-fine fibers, as described in U.S. Pat. Nos. 3,531,368 and 3,350,488. By such a process, fibers with a common thickness at the time of the formation of a multi-layer tubular woven fabric can be made into ultra-fine fibers at a later process. Consequently, troubles that may occur during various processing, for example, breakage of a yarn and formation of lint during the weaving process or during various yarn processing before weaving, are minimized.

The vascular prosthesis is preferably a double-layer woven vascular prosthesis formed by weaving two layers together by well-known technique such as binding of the inner layer with the warp, binding of the inner layer with the weft, and binding with the multiple wefts. Double-layer woven structure is advantageous because there is no need for a bonding process of two woven fabrics by lamination or sewing, and moreover the two layers jointed together by the warp or weft can serve as a vascular prosthesis with high flexibility and high mechanical strength.

Various types of organic fibers may be used as the fibers forming the vascular prosthesis, but preferred in terms of the water absorptivity and the degradation resistance are polyester fibers. Examples of the polyester fibers include polyethylene terephthalate fibers, polybutylene terephthalate fibers and the like. The polyester fibers may be copolymerized polyester fibers produced by copolymerizing polyethylene terephthalate or polybutylene terephthalate with an acid component, for example, isophthalic acid, sodium 5-sulfoisophthalate, or an aliphatic dicarboxylic acid such as adipic acid. The fibers contained in the multifilament yarn may be a single type or an appropriate combination of different types of fibers.

The loom to be used may be a water-jet loom, an air-jet loom, a rapier loom, a shuttle loom and the like. Of these, preferred is a shuttle loom, which is excellent in weaving a tubular fabric and can give a uniform tubular structure. The weave pattern of the double-layer woven vascular prosthesis may be plain weave, twill weave or sateen weave, or modified weave thereof, or multi-layer weave. The basic weaving process for producing the vascular prosthesis may be a known process.

The vascular prosthesis can be used for applications involving loading of an antithrombotic agent on a vascular prosthesis. The antithrombotic agent loaded on the vascular prosthesis may be, for example, an organism-derived anticoagulant such as heparin, low-molecular-weight heparin, urokinase, and hirudin; a synthetic anticoagulant and a synthetic antiplatelet such as argatroban, warfarin, acetylsalicylic acid, ticlopidine and the like. The vascular prosthesis may be loaded with a hydrophilic polymer such as polyethylene glycol, polyvinyl alcohol, and polyvinylpyrrolidone. The loading may be performed by any method, and may be done by, for example, coating the surface of the multifilament yarn with a solution containing the above drug or polymer; or fixing the drug or polymer on the surface of the multifilament yarn through chemical reaction such as condensation reaction, using a reactive functional group chemically introduced into the drug or polymer; or fixing the drug or polymer by radical reaction using a high energy beam; or filling the voids in the multifilament yarn with the drug or polymer through impregnation of the yarn with collagen, gelatin or hydrogel containing the drug or the polymer; or other methods. The loading of an ionic compound such as heparin, may be done by, for example, coating the surface of the multifilament yarn with a salt of the ionic compound formed with a counterion, or binding the counterion of the ionic compound to the surface of the multifilament yarn and then binding the ionic compound to the counterion by ionic interaction. In terms of imparting high antithrombotic activity and stably maintaining the antithrombotic activity for a long period of time, preferred are fixing of the drug or polymer on the surface through chemical reaction using a reactive functional group chemically introduced into the drug or polymer, and binding of the counterion of the drug or polymer to the surface followed by ionic binding of the drug or polymer to the counterion. Loading the drug or polymer on the multifilament yarn, as described above, to impart antithrombotic activity may be performed before formation of the tubular woven fabric. However, antithrombotic activity is preferably imparted after formation of a composite tubular woven fabric in view of reduction in production cost.

The vascular prosthesis can be used for applications involving preclotting.

EXAMPLES

Our protheses will be specifically described with reference to Examples, but this disclosure is not limited thereto. Various alterations and modifications are possible within the technical scope of the disclosure. The various types of the properties evaluated in the Examples were measured as follows.

Measurement Methods (1) Monofilament Fineness

The total fineness of a yarn was determined as a mass-corrected fineness in accordance with method A in JIS L 1013 (2010) 8.3.1, by setting the predetermined load at 0.045 cN/dtex. The determined total fineness was divided by the number of monofilaments to give a monofilament fineness.

(2) Average Intersecting Angle S of Microfiber Monofilaments

A produced tubular woven fabric was cut open in the longitudinal direction. The inner wall surface was photographed at 400-fold magnification with a microscope VHX-2000 (KEYENCE CORPORATION). In the photograph, one microfiber multifilament yarn was arbitrarily selected from each of the warp and weft. In the selected yarn, intersecting angles formed by adjacent microfiber monofilaments were examined. A relatively large intersecting angle of the monofilaments was selected and the angle (0° to 90°) was measured. In total, five large intersecting angles were determined and the mean value was calculated. The mean value of the intersecting angles was determined on other arbitrarily selected areas, and in total three areas were examined. The obtained mean values from the three areas were further averaged to determine an average intersecting angle S.

Whether an intersecting angle of 25° or more is frequently observed is important. Therefore, when an intersecting angle of 25° or more was not observed at all in the arbitrarily selected two filament yarns, the measurement was omitted and the results were reported as "no intersection." When at least one intersecting angle of 25° or more was found in the arbitrarily selected two filament yarns, five relatively large intersecting angles were selected from intersecting angles that include those of 25° or less, and the intersecting angles were measured and averaged.

(3) Cover Factor

The cover factor (CF) is a value calculated from the total fineness and density of the warp yarn or the weft yarn in the fabric. The cover factor is expressed by the following formula:

$$CF = (Dw \times 0.9)^{1/2} \times Nw + (Df \times 0.9)^{1/2} \times Nf,$$

where Dw is the total fineness of the warp yarn (dtex), Df is the total fineness of the weft yarn (dtex), Nw is the density of the warp yarn in the fabric (yarn/2.54 cm), and Nf is the density of the weft yarn in the fabric (yarn/2.54 cm).

The density of the yarns in the fabric was determined as follows. A produced tubular woven fabric was cut open in the longitudinal direction. The inner wall surface was photographed at 50-fold magnification with a microscope VHX-2000 (KEYENCE CORPORATION) and the numbers of the yarns were counted.

(4) Cell Settlement

A produced vascular prosthesis was cut open and, from the opened prosthesis, a disk-shaped sample of 15 mm in diameter was cut out with a blanking punch. One sheet of the disk-shaped sample of the vascular prosthesis was placed, with the inner wall surface facing up, in a well of a 24-well microplate for cell culture (Sumitomo Bakelite Co., Ltd.). A pipe-shaped metal weight with a wall thickness of 1 mm was placed on the sample. Normal human umbilical vein endothelial cells (Takara Bio, Inc.) were suspended in 2% FBS (fetal calf serum) Endothelial Cell Growth Medium 2 Kit (Takara Bio, Inc.) and added at $5 \times 10^4$ cells per well. After incubation at 37° C. for 24 hours, the sample was rinsed with PBS (phosphate buffered saline) (−) (Nissui Pharmaceutical Co., Ltd.). The number of adherent cells were measured using MTT assay kit (Dojindo Laboratories). Separately, the adherent cells were fixed in 10% formalin solution (Wako Pure Chemical Industries, Ltd.) and subjected to morphology examination with a scanning electron microscope (Hitachi High-Technologies Corporation).

(5) Kink Resistance

The kink resistance was evaluated in terms of the kink radius in accordance with the guidance of ISO 7198. Briefly, a tubular woven fabric was formed into a loop, and the radius of the loop was gradually decreased until apparent kinking occurred. A cylindrical mandrel with a known radius was placed in the loop to measure the radius (kink radius). In the test, internal pressure was not applied for the purpose of the evaluation of the genuine kink resistance of the tubular woven fabric.

Example 1

A polyester microfiber multifilament yarn with a monofilament fineness of about 0.23 dtex and a total fineness of 33 dtex was prepared, and used as warp and weft yarns to form the inner layer of a tubular woven fabric in the weaving process described later.

A polyester multifilament yarn with a monofilament fineness of about 2.25 dtex and a total fineness of 56 dtex was prepared as a warp yarn, then a polyester monofilament yarn with a monofilament fineness of 33 dtex was prepared as a weft yarn, and the warp and weft yarns were used to form the outer layer of the tubular woven fabric.

A tubular woven fabric with plain weave double-layer design in which two sets of the warp and weft yarns were arranged in the both layers were woven with a shuttle loom using the above yarns. The obtained tubular fabric with 3 mm in internal diameter was scoured at 98° C. The fabric was dry-heated at 120° C. Into the fabric, a rod mandrel was inserted and the fabric was heat-set at 170° C. into that shape. The fabric was sterilized. The produced tubular woven fabric was subjected to an evaluation of cover factor, average intersecting angle S, cell settlement, and kink resistance. The results are shown in Table 1. In the measurement of the average intersecting angle S, no intersecting angle of 25° or more was found in the observed areas and reported as "no intersection." The cell settlement was very good, and a desired level of kink resistance required of the vascular prosthesis was observed.

Example 2

A tubular woven fabric was produced in the same manner as in Example 1, except that the warp of the inner layer was formed by alternately arranging two types of yarns, a polyester microfiber multifilament yarn with a monofilament fineness of about 0.23 dtex and a total fineness of 33 dtex and a polyester multifilament yarn with a monofilament fineness of about 1.38 dtex and a total fineness of 33 dtex (the amount (%) of the microfiber multifilament yarn in the warp: 50% by weight); and that the weft of the inner layer was formed with a microfiber multifilament yarn with a monofilament fineness of about 0.23 dtex and a total fineness of 33 dtex (the amount (%) of the microfiber multifilament yarn in the weft: 100% by weight).

The produced tubular woven fabric was subjected to an evaluation of cover factor, average intersecting angle S, cell settlement, and kink resistance. The results are shown in Table 1. The average intersecting angle S was reported as "no intersection" as in Example 1. The cell settlement was good, and a desired level of kink resistance required of the vascular prosthesis was observed.

Example 3

A tubular woven fabric was produced in the same manner as in Example 1, except that the inner layer was produced by using, as the warp and weft yarns, a polyester microfiber multifilament yarn with a monofilament fineness of about 0.084 dtex and a total fineness of 53 dtex.

The produced tubular woven fabric was subjected to an evaluation of cover factor, average intersecting angle S, cell settlement, and kink resistance. The results are shown in Table 1. The average intersecting angle S was reported as "no intersection" as in Examples 1 and 2. The cell settlement was extremely very good and superior to that in Example 1. The kink resistance required of the vascular prosthesis was further improved as compared to that in Examples 1 and 2.

Example 4

A tubular woven fabric was produced in the same manner as in Example 1, except that after weaving and scouring, a polyethylene film (spacer) with 4 mm in width and 0.12 mm in thickness was inserted into the tubular woven fabric, then the tubular woven fabric was treated by water jet punching under the conditions of a discharge nozzle diameter of 0.25 mm, a discharge nozzle interval of 2.5 mm, and a pressure of 20 kg/cm$^2$, and the tubular woven fabric was subjected to drying, heat setting with the tubular template and sterilization.

The produced tubular woven fabric was subjected to an evaluation of cover factor, average intersecting angle S, cell settlement, and kink resistance. The results are shown in Table 1. In the measurement of the average intersecting angle S, a few intersecting angles of 25° or more were found in the observed areas, but the mean value of five intersecting angles in each of the arbitrarily selected two filament yarns did not exceed 25°, and average value S of the three areas was 17°. The cell settlement was good, and a desired level of kink resistance required of the vascular prosthesis was observed.

Example 5

A tubular woven fabric was produced in the same manner as in Example 1, except that the inner layer was produced by using, as the warp and weft yarns, a polyester microfiber multifilament yarn with a monofilament fineness of about 0.30 dtex and a total fineness of 44 dtex, and that the outer layer was produced by using, as the weft yarn, a polyester monofilament yarn with a monofilament fineness of 180 dtex.

The produced tubular woven fabric was subjected to an evaluation of cover factor, average intersecting angle S, cell settlement, and kink resistance. The results are shown in Table 1. The average intersecting angle S was reported as "no intersection" as in Examples 1, 2 and 3. The cell settlement was comparable to that in Example 1 and superior to that in Example 2. Since the monofilament yarn used as the weft yarn to form the outer layer had a monofilament fineness of 180 dtex, the kink resistance required of the vascular prosthesis resulted in an extremely very good value.

Example 6

A tubular woven fabric was produced in the same manner as in Example 3, except that the outer layer was produced by using, as the weft yarn, a polyester monofilament yarn with a fineness of 180 dtex.

The produced tubular woven fabric was subjected to an evaluation of cover factor, average intersecting angle S, cell settlement, and kink resistance. The results are shown in Table 1. The average intersecting angle S was reported as "no intersection" as in Examples 1, 2 and 3. The cell settlement was, as in Example 3, extremely very good and superior to that in Example 1. Since the monofilament yarn used as the weft yarn to form the outer layer had a monofilament fineness of 180 dtex, the kink resistance required of the vascular prosthesis resulted in an extremely very good value.

Example 7

A tubular woven fabric was produced in the same manner as in Example 1, except that the outer layer was produced by using, as the warp yarn, a polyester multifilament yarn with a monofilament fineness of about 2.25 dtex and a total fineness of 56 dtex and using, as the weft yarn, a polyester multifilament yarn with a monofilament fineness of about 1.83 dtex and a total fineness of 22 dtex.

The produced tubular woven fabric was subjected to an evaluation of cover factor, average intersecting angle S, cell settlement, and kink resistance. The results are shown in Table 1. The average intersecting angle S was reported as "no intersection" as in Example 1. The cell settlement was very good, which was comparable to that in Example 1. However, since both the warp and weft yarns used to form the outer layer were multifilament yarns, the kink resistance resulted in a larger value than that in Example 1.

Example 8

A tubular woven fabric was produced in the same manner as in Example 6, except that the fabric density of the inner layer was adjusted so that the cover factor of the inner layer defined by the warp and weft yarns was about 1900.

The produced tubular woven fabric was subjected to an evaluation of cover factor, average intersecting angle S, cell settlement, and kink resistance. The results are shown in Table 1. The average intersecting angle S was reported as "no intersection" as in Example 6. The cell settlement was, as in Example 6, extremely very good. However, since the cover factor in this Example was slightly smaller than that in Example 6, the kink resistance required of the vascular prosthesis resulted in a slightly higher value than that in Example 6.

Comparative Example 1

A tubular woven fabric was produced in the same manner as in Example 1, except that the inner layer was produced by using, as the warp yarn, a polyester multifilament yarn with a monofilament fineness of about 1.38 dtex and a total fineness of 33 dtex and using, as the weft yarn, a polyester microfiber multifilament yarn with a monofilament fineness of about 0.23 dtex and a total fineness of 33 dtex.

The produced tubular woven fabric was subjected to an measurement of cover factor, average intersecting angle S, cell settlement, and kink resistance. The results are shown in Table 1. Since no microfiber multifilament yarn was present in the warp, the average intersecting angle S was measured on two yarns arbitrarily selected from the weft. The average intersecting angle S was reported as "no intersection" as in Example 1. However, since not both the warp and weft of the inner layer contain a microfiber multifilament yarn with a monofilament fineness of 0.50 dtex or less in an amount of 50% by weight or more, the cell settlement was unsuitable for practical use. In terms of the kink resistance required of the vascular prosthesis, the value was inferior to that in Example 1.

Comparative Example 2

A tubular woven fabric was produced in the same manner as in Example 1, except that after weaving and scouring, a polyethylene film (spacer) with 4 mm in width and 0.12 mm in thickness was inserted into the tubular woven fabric, then the tubular woven fabric was treated by water jet punching under the conditions of a discharge nozzle diameter of 0.25 mm, a discharge nozzle interval of 2.5 mm, and a pressure of 80 kg/cm², and the tubular woven fabric was subjected to drying, heat setting with the tubular template and sterilization.

The produced tubular woven fabric was subjected to an evaluation of cover factor, average intersecting angle S, cell settlement, and kink resistance. The results are shown in Table 1. In the measurement of the average intersecting angle S, several intersecting angles of 25° were found in the observed areas, in particular, at least five intersecting angles of 25° were contained in the arbitrarily selected two filament yarns. The mean value of the five intersecting angles exceeded 25° in each of the three areas, and the average intersecting angles S of the three areas was 35°. In addition, as in Comparative Example 1, since not both the warp and weft of the inner layer contain a microfiber multifilament yarn with a monofilament fineness of 0.50 dtex or less in an amount of 50% by weight or more, cell settlement was unsuitable for practical use. In terms of the kink resistance required of the vascular prosthesis, the value was inferior to that in Example 1.

Comparative Example 3

A tubular woven fabric was produced in the same manner as in Example 1, except that the fabric density of the inner layer was adjusted so that the cover factor of the inner layer defined by the warp and weft yarns was about 1700.

The produced tubular woven fabric was subjected to measurement of cover factor, average intersecting angle S, cell settlement, and kink resistance. The results are shown in Table 1. In the measurement of the average intersecting angle S, a few intersecting angles of 25° or more were found in the observed areas, but the mean value of five intersecting angles in each of the arbitrarily selected two filament yarns did not exceed 25°, and the average value S of the three areas was 18°. Since the fabric density was low and the cover factor was 1700, the cell settlement resulted in an unsuitable level for practically use. In terms of the kink resistance required of the vascular prosthesis, the value was at the same level as that in Example 1.

TABLE 1

|  | Cover factor | Average intersecting angle S | Cell settlement | Kink resistance Evaluation | Measurement value |
|---|---|---|---|---|---|
| Example 1 | 2550 | No intersection | Very good | Good | 50 mm |
| Example 2 | 2400 | No intersection | Good | Good | 55 mm |
| Example 3 | 2100 | No intersection | Extremely very good | Very good | 45 mm |
| Example 4 | 2550 | 17° | Good | Good | 55 mm |
| Example 5 | 2200 | No intersection | Very good | Extremely very good | 22 mm |
| Example 6 | 2200 | No intersection | Extremely very good | Extremely very good | 16 mm |
| Example 7 | 2550 | No intersection | Very good | Good | 75 mm |
| Example 8 | 1900 | No intersection | Extremely very good | Extremely very good | 26 mm |
| Comparative Example 1 | 2100 | No intersection | Poor | Good | 70 mm |
| Comparative Example 2 | 2150 | 35° | Poor | Good | 90 mm |
| Comparative Example 3 | 1700 | 18° | Poor | Good | 50 mm |

INDUSTRIAL APPLICABILITY

We provide a suitable vascular prosthesis used in various surgical operations.

The invention claimed is:

1. A vascular prosthesis with tubular woven structure, the prosthesis comprising an inner layer adapted to contact a blood flow, the inner layer being formed of warp and weft yarns and having a cover factor of 1800 or more, each of a warp and weft yarns comprising a microfiber multifilament yarn with a monofilament fineness of 0.50 dtex or less, the multifilament yarn comprising microfiber monofilaments having an average intersecting angle S of the monofilaments of less than 25°,
wherein the tubular woven structure comprises two or more layers, and one or more of the layers other than the inner layer comprise a multifilament yarn with a monofilament fineness of 1.0 dtex or more in the warp; and
the average intersecting angle S can be obtained: 1) a produced tubular woven structure is cut open in a longitudinal direction, and the inner wall surface is photographed at 400-fold magnification with a microscope and, in the photograph, one microfiber multifilament yarn is arbitrarily selected from each of warp and weft yarns and, in the selected yarn, intersecting angles formed by adjacent microfiber monofilaments are examined, and a relatively large intersecting angle of the monofilaments is selected and an angle (0° to 90°) is measured and, in total, five large intersecting angles are determined and the mean value calculated, and the mean value of the intersecting angles is determined on other arbitrarily selected areas and, in total, three areas are examined, and the obtained mean values from the three areas are further averaged to determine the average intersecting angle S.

2. The vascular prosthesis of claim 1, wherein the microfiber multifilament yarn are present in an amount of 50% by weight or more in each of the warp and weft.

3. The vascular prosthesis of claim 2, wherein the cover factor defined by the warp and weft yarns forming the inner layer is 2000 or more.

4. The vascular prosthesis of claim 2, wherein the tubular woven structure comprises two or more layers, and one or more of the layers other than the inner layer comprise a multifilament yarn with a monofilament fineness of 1.0 dtex or more in the warp.

5. The vascular prosthesis of claim 3, wherein the tubular woven structure comprises two or more layers, and one or more of the layers other than the inner layer comprise a multifilament yarn with a monofilament fineness of 1.0 dtex or more in the warp.

6. The vascular prosthesis of claim 2, wherein the tubular woven structure comprises two or more layers, and one or more of the layers other than the inner layer comprise a monofilament yarn with a monofilament fineness of 20.0 dtex or more in the weft.

7. The vascular prosthesis of claim 3, wherein the tubular woven structure comprises two or more layers, and one or more of the layers other than the inner layer comprise a monofilament yarn with a monofilament fineness of 20.0 dtex or more in the weft.

8. The vascular prosthesis of claim 4, wherein the tubular woven structure comprises two or more layers, and one or more of the layers other than the inner layer comprise a monofilament yarn with a monofilament fineness of 20.0 dtex or more in the weft.

9. The vascular prosthesis of claim 1, wherein the cover factor defined by the warp and weft yarns forming the inner layer is 2000 or more.

10. The vascular prosthesis of claim 9, wherein the tubular woven structure comprises two or more layers, and one or more of the layers other than the inner layer comprise a multifilament yarn with a monofilament fineness of 1.0 dtex or more in the warp.

11. The vascular prosthesis of claim 9, wherein the tubular woven structure comprises two or more layers, and one or more of the layers other than the inner layer comprise a monofilament yarn with a monofilament fineness of 20.0 dtex or more in the weft.

12. The vascular prosthesis of claim 1, wherein the tubular woven structure comprises two or more layers, and one or more of the layers other than the inner layer comprise a monofilament yarn with a monofilament fineness of 20.0 dtex or more in the weft.

* * * * *

UNITED STATES PATENT AND TRADEMARK OFFICE
CERTIFICATE OF CORRECTION

PATENT NO. : 10,070,949 B2
APPLICATION NO. : 15/100109
DATED : September 11, 2018
INVENTOR(S) : Tsuchikura et al.

Page 1 of 1

It is certified that error appears in the above-identified patent and that said Letters Patent is hereby corrected as shown below:

In the Claims

In Column 14, at Line 17, please change "claim 9" to -- claim 3 --; and at Line 22, please change "claim 9" to -- claim 3 --.

Signed and Sealed this
Twenty-seventh Day of August, 2019

Andrei Iancu
*Director of the United States Patent and Trademark Office*